(12) United States Patent
Mastronardi et al.

(10) Patent No.: US 8,690,427 B2
(45) Date of Patent: Apr. 8, 2014

(54) METHODS FOR HIGH ENERGY X-RAY IMAGING USING REMOTELY-ALIGNED ARCUATE DETECTOR ARRAY

(71) Applicant: American Science and Engineering, Inc., Billerica, MA (US)

(72) Inventors: Richard Mastronardi, Medfield, MA (US); Jeffrey M. Denker, Woburn, MA (US); Peter Rothschild, Newton, MA (US); Dan-Cristian Dinca, Billerica, MA (US); Aaron D. Pailes, Acton, MA (US); David R. Blake, Georgetown, MA (US); Domenic Martignetti, Nashua, NH (US)

(73) Assignee: American Science and Engineering, Inc., Billerica, MA (US)

( * ) Notice: Subject to any disclaimer, the term of this patent is extended or adjusted under 35 U.S.C. 154(b) by 0 days.

(21) Appl. No.: 13/865,382

(22) Filed: Apr. 18, 2013

(65) Prior Publication Data
US 2013/0230140 A1 Sep. 5, 2013

Related U.S. Application Data

(63) Continuation of application No. 13/235,894, filed on Sep. 19, 2011, now Pat. No. 8,439,565.

(60) Provisional application No. 61/393,481, filed on Oct. 15, 2010, provisional application No. 61/414,482, filed on Nov. 17, 2010.

(51) Int. Cl.
*A61B 6/08* (2006.01)
*H05G 1/26* (2006.01)

(52) U.S. Cl.
USPC .............................. 378/205; 378/57; 378/98.8

(58) Field of Classification Search
USPC ................................. 378/4, 19, 57, 98.8, 205
See application file for complete search history.

(56) References Cited

U.S. PATENT DOCUMENTS

| 5,768,331 A | 6/1998 | Gordon et al. ................... 378/19 |
| 6,203,197 B1 | 3/2001 | Peter .............................. 378/205 |
| 7,103,137 B2 | 9/2006 | Seppi et al. ....................... 378/9 |
| 7,526,064 B2 | 4/2009 | Akery .............................. 378/57 |

(Continued)

OTHER PUBLICATIONS

Kim, Sang Wook *Authorized officer* Korean Intellectual Property Office, *International Search Report and Written Opinion of the International Searching Authority*—Application No. PCT/US2011/052130, dated Feb. 17, 2012 (7 pages).

(Continued)

*Primary Examiner* — Thomas R Artman
(74) *Attorney, Agent, or Firm* — Sunstein Kann Murphy & Timbers LLP

(57) ABSTRACT

Methods for inspecting contents of a container. High-energy penetrating radiation collimated into a fan beam illuminates an inspected container from one side, while a plurality of detector plates are disposed on the opposite side of the container. Each detector plate has a plurality of detector modules, each of which, in turn, is disposed on a remotely activated alignment and has multiple detector elements. A controller governs the orientation of each of the plurality of detector plates based at least on the detector signal generated by its detector elements such that each detector element of each detector module of each detector plate may be aligned to within a specified fraction of the transverse dimension of the fan beam as measured at the exit slot.

4 Claims, 4 Drawing Sheets

(56) References Cited

U.S. PATENT DOCUMENTS

| | | |
|---|---|---|
| 7,581,885 B2 | 9/2009 | Ertel et al. .................... 378/206 |
| 7,720,195 B2 | 5/2010 | Allman et al. ................. 378/57 |
| 7,952,079 B2 * | 5/2011 | Neustadter et al. ........... 250/393 |
| 8,254,519 B2 | 8/2012 | Sugita et al. ................... 378/22 |
| 2004/0008810 A1 | 1/2004 | Nelson et al. .................. 378/19 |
| 2004/0017887 A1 | 1/2004 | Le et al. .......................... 378/57 |
| 2006/0256914 A1 | 11/2006 | Might et al. .................... 378/57 |
| 2008/0112541 A1 | 5/2008 | Hardesty ...................... 378/205 |
| 2008/0226035 A1 | 9/2008 | Masuda et al. ................ 378/145 |
| 2009/0147913 A1 | 6/2009 | Dragon et al. .................. 378/57 |
| 2011/0013752 A1 | 1/2011 | Takahashi ..................... 378/205 |
| 2012/0076257 A1 | 3/2012 | Star-Lack et al. ................. 378/4 |
| 2012/0093288 A1 | 4/2012 | Mastronardi et al. ........... 378/57 |

OTHER PUBLICATIONS

Insea S.A., *Roboscan 1M*—http:www.inseasa.gr/page/show/9/en, Dec. 2010 (10 pages).

* cited by examiner

METHODS FOR HIGH ENERGY X-RAY IMAGING USING REMOTELY-ALIGNED ARCUATE DETECTOR ARRAY

The present application is a continuation application of copending U.S. patent application Ser. No. 13/235,894, filed Sep. 19, 2011 and issued as U.S. Pat. No. 8,439,565. Like that application, the present application claims the priority of U.S. Provisional Patent Application Ser. No. 61/393,481, filed Oct. 15, 2010, and of U.S. Provisional Patent Application Ser. No. 61/414,482, filed Nov. 17, 2010. All of the aforesaid applications are incorporated herein by reference.

TECHNICAL FIELD

The present invention relates to systems and methods for detecting high-energy penetrating radiation, and more particularly to the application of such systems and methods to the inspection of cargo and cargo-carrying vehicles with high-energy x-rays.

BACKGROUND ART

X-ray security inspection systems for cargo and shipping containers typically use transmission radiographic techniques. A high inspection throughput of cargo and cargo-carrying vehicles is at a premium. Consequently, it is desirable that an entire plane through the cargo be probed simultaneously, and one inspection modality employs a fan-shaped beam to produce images of a target object while the fan beam and detectors are moved relative to the object. Alternatively, the object may be moved in a direction substantially perpendicular to the plane of the fan beam. In cases where illumination is provided by a fan beam of x-ray radiation, useful spatial resolution of contents of the inspected object is typically provided by a plurality of detector elements. The spatial pixel resolution is governed by the dimensions of the detector elements in a plane normal to the propagation direction of the beam, or else by post-collimators limiting the field of view of each detector element.

In cargo imaging applications, it may be necessary for the penetrating radiation to penetrate a significant thickness of highly attenuating material, and a requirement for penetration of more than 300 mm of steel equivalent is not unusual. As used herein, a penetration depth quoted in length of steel equivalent refers to the maximum steel thickness behind which a lead block can still be seen. For thicknesses of steel exceeding the penetration capacity of a particular imaging system, the image will be completely dark, and the block will not be seen.

To ensure the required penetration, inspection systems employed for the inspection of cargo, and in certain industrial applications, typically use x-rays with a maximum energy of several MeV, and, more particularly, in current systems, energies up to about 9 MeV. As used herein and in any appended claims, energies in excess of 1 MeV may be referred to as hard x-rays or high-energy x-rays.

Detector modules used in high energy x-ray transmission imaging systems require precise alignment relative to the centerline of the beam plane to optimize the imaging capability of the equipment. This is traditionally done using a combination of precision control surfaces on the base structure and manual adjustors to position the detector element.

As an example of an alignment requirement, consider a system in which a resolution of 15 mm is required of a voxel situated 4 m from the source of radiation. Say the detector elements are located at a distance of 8 m from the source, thereby allowing the imaging of a cargo vehicle having a cross section of 3 m width by 5 m height. Since it is the nature of Bremsstrahlung that x-ray generation at the target is more sharply forward-peaked for higher energies, the beam will become more narrowly peaked as it hardens on propagation through attenuating matter in the inspected object. One might assume that the detector must be centered on the beam to within half the dimension of a resolution element, or, say, 10 mm at 8 m. For scale, a resolution requirement of 10 mm at a distance of 8 m is an angular tolerance of resolution of 1.25 mr (0.07°), or comparable to the width of the eye of a 9/65 sewing needle at a distance of 8 inches from a tailor's eye—a formidable task, when considering that each of an array of nearly 1800 detector elements must be aligned to that accuracy in each of two dimensions in order to provide uniform resolution across the image field.

In ordinary alignment practice, x-ray detection tools, such as small ion chambers, may be used to coarsely measure the beam profile and locate the position near the detector module array. Then a variety of optically based tools (laser modules, surveyor's transit, digital levels, etc.) are employed to assist the technician to position the modules to the expected beam location. Due to the nature of ionizing radiation, the technician performing the alignment should not be near the equipment while the source is energized. Therefore, the manual adjustments are never made with the beam on, and no direct feedback of how well the detector is aligned while the changes are being made is available. Moreover, the process is made substantially more arduous if the geometry of the system is anything other than rectilinear.

Since there are many sources of error in each of the measurements taken and adjustments made, the alignment process is in essence a "trial and error" based iterative method. The time consuming nature of the process results in a labor intensive effort that can be quite costly and ultimately the detectors may not end up in an optimal position. Since the use of optical alignment tools requires line of sight from the various components in order to function, the alignment process can require the removal of covers to gain access to the detectors and adjustors and may expose the detectors and other sensitive components within the equipment to potentially damaging environmental factors.

X-ray detector modules may also incorporate a variety of post collimators mounted directly in front of the detector elements of the detector modules in order to reject in-plane and out of plane noise sources, such as scattered radiation, from reaching the detector elements. The incorporation of these technologies makes the detector modules more sensitive to misalignment than traditional detector modules, and, if the geometry of the system is non-rectilinear, the alignment is all the more difficult.

For practical and effective deployment, an x-ray inspection system must provide for alignment in the field at the time of installation as well as for ready realignment to minimize down time. As systems are required to provide increasingly higher resolution and larger scan areas, the number of detector elements increases, and the sensitivity to misalignment increases as well. Non-rectilinear geometries make the process all the more arduous. All of these factors make the process of alignment much more critical to the ultimate performance of the machine than may be accommodated using existing means that are known in the art.

SUMMARY OF EMBODIMENTS OF THE INVENTION

In accordance with various embodiments of the present invention, methods and apparatus are provided for inspecting large objects by x-ray transmission by means of a curvilinearly disposed array of detectors coaligned to a single source of penetrating radiation by active alignment of detector plates during the course of irradiation by the source itself.

In accordance with one embodiment of the invention, a scanning system is provided for inspecting contents of an inspected container. The scanning system has a source of penetrating radiation of peak energy exceeding 1 MeV and a collimator having an exit slot for forming the penetrating radiation into a fan beam characterized by a transverse dimension as measured at the exit slot. A plurality of detector plates are arcuately disposed at a distance exceeding 5 meters from the source of penetrating radiation, where each detector plate has a plurality of detector modules. Each detector module, in turn, has a plurality of detector elements, each detector element generating a detector signal corresponding to that detector element. Each detector module is disposed on a remotely activated alignment plate, which may be identical to the detector plate. Finally, the scanning system has a controller for governing orientation of each of the plurality of alignment plates based at least on the detector signal generated by that detector element, such that each detector element of each detector module of each detector plate may be aligned to within a specified fraction of the transverse dimension of the fan beam as measured at the exit slot.

In other embodiments of the invention, the scanning system may also have a propulsion mechanism for moving the source, the collimator and the plurality of detector elements with respect to the container in a direction substantially transverse to the fan beam. The source of penetrating radiation may be a linac.

In yet other embodiments, the controller may include a current-integrating electronics module. The detector elements may be separated from at least one other detector of the plurality of detector elements by means of a vane. The remotely activated alignment plate may include a plurality of actuators.

In accordance with alternate embodiments of the invention, a method may be provided for deriving one or more specified characteristics of an inspected object. The method has steps of:
 a. aligning a plurality of detector modules, each of the detector modules of the plurality of detector modules comprising a plurality of detector elements, and each of the detector modules disposed on an alignment plate, the step of aligning performed on the basis of a detection signal generated by each of the detector elements due to activation of a single source of energetic particles;
 b. irradiating the inspected object with a plurality of pulses of penetrating radiation;
 c. detecting the penetrating radiation after traversal of the inspected object thereby and generating an imaging signal; and
 d. processing the imaging signal to derive an image of the inspected object.

BRIEF DESCRIPTION OF THE DRAWINGS

The foregoing features of the invention will be more readily understood by reference to the following detailed description, taken with reference to the accompanying drawings, in which.

DETAILED DESCRIPTION OF EMBODIMENTS OF THE INVENTION

In an x-ray transmission imaging system, sensitivity and resolution may be limited by scattered radiation that impinges upon a detector element other than directly from the source through the inspected object. Scattered radiation impinging upon a detector element effectively raises the noise floor above which transmitted radiation must be detected.

Figure 1:
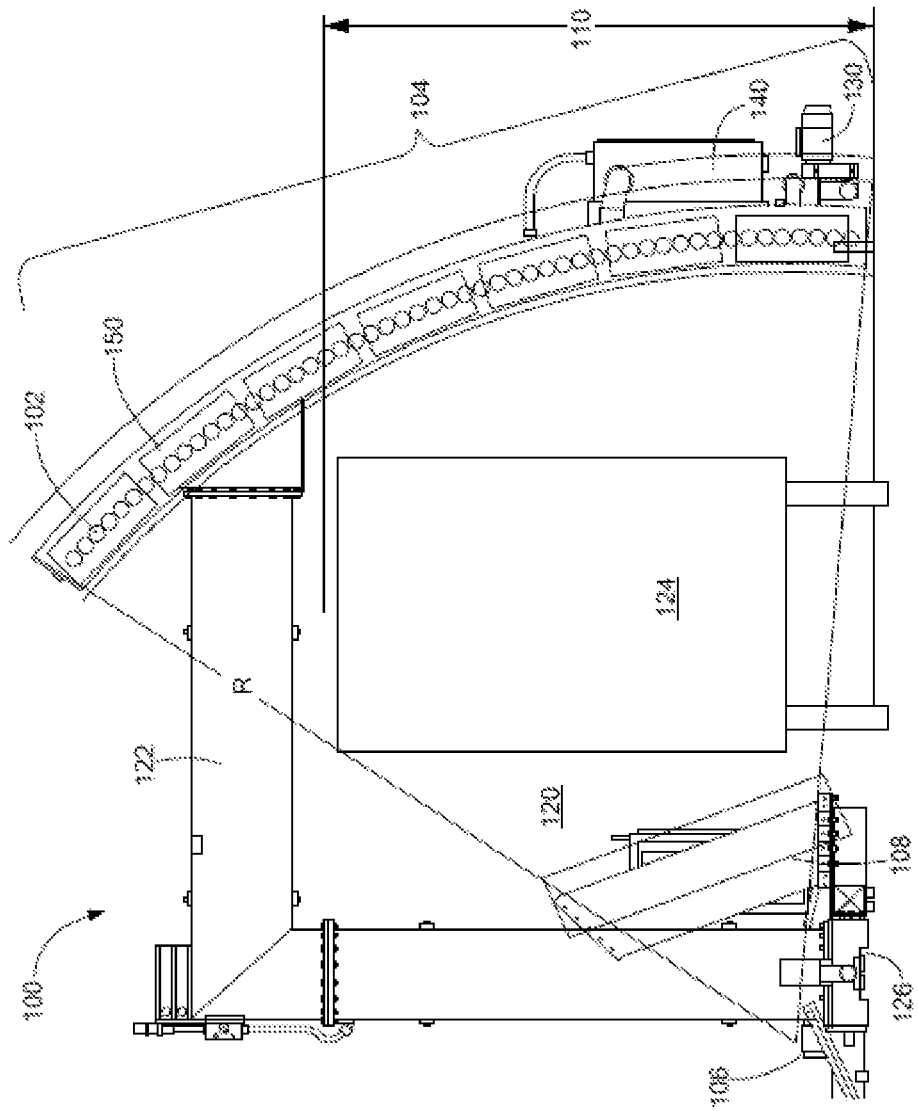
FIG. 1 schematically illustrates an x-ray inspection system with arcuately aligned detectors in accordance with embodiments of the present invention.

In accordance with preferred embodiments of the present invention, an x-ray inspection system, designated generally by numeral 100, is provided, as now described with reference to FIG. 1. In x-ray scanning system 100, a plurality of detector modules 102 are arrayed in a curvilinear configuration, represented in FIG. 1 by arc 104. Arc 104 forms a portion of a circle, such that all detector elements comprising each of the modules receive radiation directed from an x-ray source 106, but all of the detector elements are substantially immune to scatter radiation arising at other detectors or elsewhere within the system.

Source 106 emits penetrating radiation, typically x-rays at a spectrum of energies up to 9 MeV, typically by acceleration of electrons in a linac incident upon a metallic target (not shown) and subsequent Bremsstrahlung emission from the target. The endpoint energy typically exceeds 1 MeV, and multiple endpoint energies may be employed within the scope of the present invention. X-rays emitted by source 106, typically in pulses on the order of microseconds, are collimated into a fan beam 120 by x-ray beam forming mechanism 108, shown as a collimator, typically formed of lead with an exit slot characterized by a gap on the order of 1 cm in width.

In a preferred embodiment of the invention, a multi-component x-ray beam forming mechanism optimizes parameters of beam flatness and x-ray beam dimension. The narrower the X-ray beam, the smaller the dose to cargo and amount of unwanted scattered x-rays. The mechanism is composed of at least two collimators. A first collimator stops the radiation outside of a slit opening. The dimensions of the first collimator are chosen such that the beam profile created at the detector column is flat relative to the size of the detector acceptance width/opening. A downstream collimator, or, alternatively, a set of collimators, is employed to cut from the x-ray beam created by the first collimator only the central portion.

Detector modules 102 are arrayed on plates 150, as further described below, and disposed arcuately about source 106. In a preferred embodiment, detector modules 102 cover a circular arc 104 having a circular extent of approximately 50°. Arc 104 is disposed at a radius R of approximately 8 m so as to allow gantry 122, rigidly coupling source and detector modules 102, to be propelled over inspected cargo 124, which may include one or more vehicles, or one or more cargo containers, for example. The height 110 of inspected cargo 124 may extend, in the embodiment shown in FIG. 1, as high as 5 m. Detector signals derived from detector elements of each of the detector modules are combined to derive an imaging signal, combined by controller 140 to yield an image of the contents of inspected cargo 124 or else other desired characteristics of the contents, as known in the art.

Propulsion mechanism 130, which may be an electric motor, for example, propels gantry 122 in a direction transverse to fan beam 120 so that the length of cargo 124 may be scanned by inspection system 100, also referred to herein, and in any appended claims, as scanning system 100. Gantry 122 may be propelled on rails 126, typically extending between 100-200 feet in length, such that a number of cargo containers 124 may be scanned in a single pass of gantry 122. Alternatively, gantry 122 may remain stationary while cargo 124 is propelled past gantry 122 by some other means of propulsion. Gantry 122 is preferably propelled at a rate of about 0.3 m/s, such that a scanning throughput of 25 40-foot cargo containers per hour may be achieved.

Gantry 122 is preferably designed such that the detector array remains aligned to the x-ray beam within +/−1 mm. The beam width at the detector is preferably characterized by a substantially flat intensity profile over approximately 10 mm. High quality image quality is achieved as long as each detector (of nominal 6-mm width) lies within the flat portion of the beam intensity profile This requirement allows +/−2 mm for relative motion of the structure to the x-ray beam and initial alignment to the center of the beam. An error margin of ±1 mm is allocated for structural deflections and ±1 mm for initial alignment.

Figure 2:
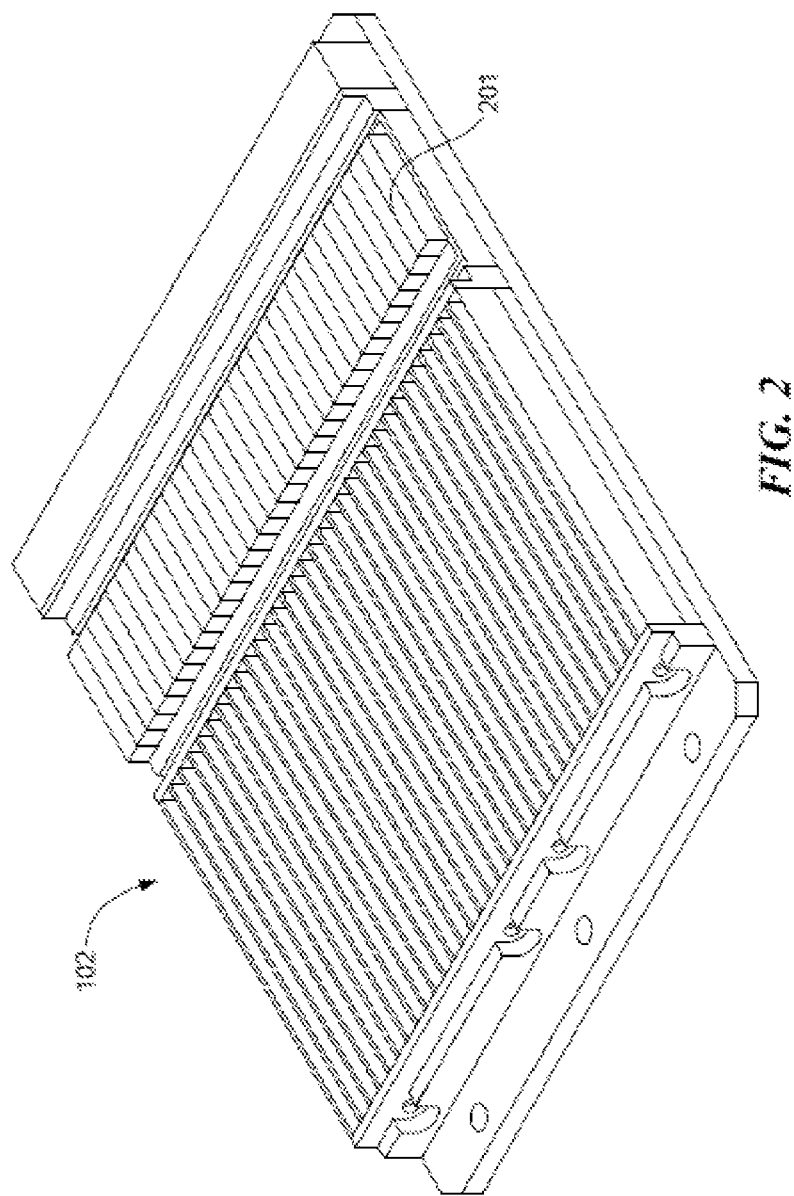
FIG. 2 shows a detector module with multiple detector elements separated by vanes, in accordance with embodiments of the present invention.

Referring now to FIG. 2, each detector module 102 includes a plurality of detector elements 201, of which, in a preferred embodiment of the invention, there are 32 per detector module. Each detector element 201 includes a scintillation crystal for converting a detected x-ray into one or more photons that are detected by a photodetector to create a detection signal, as well known in the art of x-ray detection. Individual detector elements are separated from one another by a vane that is opaque to visible light and electrons, so as to prevent cross-talk among the detector elements due to scatter, or multiple-scatter events. The opaque vane may be comprised of an x-ray absorbing sheet of tungsten, or other absorbing material.

A beam dump is provided that is separated into multiple components. One component is placed as close to the detector crystals as possible. This component fulfills two major roles. One is to prevent backscattered x-rays from producing unwanted signal in the nearby crystals and the other is to prevent low energy backscatter from the rest of the beam dump components from reaching any crystal. The other components of the beam dump are placed as far away as possible from the primary component in order to minimize the solid angle covered by the backscattered x-rays.

A typical detector element 201 consists of a volume of a light-transparent scintillation medium optically coupled to one or more photodetectors, each, usually a photomultiplier tube or a solid state photodetector. A detector medium is chosen, using design criteria known in the art, from among any materials now known, or discovered in the future, to be useful for such detection purposes. These may include optically transparent media such as glasses, plastics, etc., or crystals of alkali halides, bismuth germanate (BGO), often respectively doped with suitably high-cross-section dopants, such as rare earth oxides or sulfates, organic scintillants, etc., known to enhance scintillation. Common scintillants include $PbF_2$, bismuth germanate (BGO), lead fluoride ($PbF_2$), lead tungstate (PbWO, or "PWO"), all provided here, as examples, without limitation. One or more photodetectors (not shown) are provided to detect emission, in appropriate portions of the electromagnetic spectrum, indicating processes that convert the kinetic energy of charged particles into light.

The electrical signal output of each photodetector associated with each detector element is coupled to processor electronics 140 which may include a signal conditioning module such as a photon-counting mode electronics module, or integrating module, etc., in all cases generating an output signal A plurality of detector modules 102, preferably 8 in number, are mounted on each of a plurality, preferably 7, of detector plates (or alignment plates, which may be identical to the detector plates) 150. Each detector plate 150 serves as a detector substructure that may be positioned, by one or more actuators, relative to gantry 122.

More particularly, detector modules 102 can be adjusted while an x-ray source 106, or other source of energetic particles, is energized. "Energetic particles" refer, herein, to particles, whether massive or massless, that are typically precluded from irradiation in the vicinity of personnel for reasons of safety. The arrangement of the actuators and their connection to the detector modules permits the detector modules to be translated and rotated along their most sensitive alignment axes and hence positioned with respect to the actual position of the beam plane using their own signal as feedback. The fine incremental positioning ability of high reduction linear actuators may advantageously permit much finer adjustments than could be made by a technician; moreover, such adjustments may be executed much faster.

By directly using the response of individual detectors to the signal as they are adjusted relative to the beam, all of the measurement inaccuracies associated with mounting and taking measurements from using separate alignment devices and tools, and translating those measurements into discrete adjustments of the detectors, are effectively eliminated. Moreover, alignment may be performed readily upon installation of inspection system 100 at a site.

Through the use of a graphical user interface, the technician can perform an alignment remotely and see the results of the adjustment in real time. Another capability of the system, in addition to optimizing the detector module alignment, can be realized by sweeping the detector modules through the beam. As the detector module, or group of modules, are translated or rotated though the beam path, an accurate measurement of the beam profile can be made and the width and symmetry of the beam can be used to assess the quality of the beam formation components.

The arrangement of the three linear actuators and three spherical fixations provide three pure degrees of freedom (namely, a translation and two rotations) in the orientations most useful to align the detector module(s), while providing rigidity in the other three degrees of freedom. The use of live beam feedback from the detector ensures that the detector elements are placed in their optimum position without extrapolation. The ability of the actuators to provide pure translation of the detector elements perpendicular to the x-ray beam, whether the detector group that is being moved is parallel to the expected beam plane or intentionally rotated with respect to the beam plane, permits the detector array to be utilized as a beam profile measurement device.

The capacity of detector alignment systems in accordance with the present invention to characterize the collimated x-ray beam shape may additionally provide vital information about the quality of the beam formation system. If the beam profile and location is within expected limits, the detector array alignment can be completed. If issues with the beam profile and location are determined, the detector alignment system can be used to monitor and assess additional alignment operations to the source and primary beam formation components.

The translational degree of freedom is limited only by the available stroke of the linear actuators minus that consumed by rotations. The rotational degrees of freedom are limited by lateral binding that could develop within the actuators. By incorporating an additional degree of compliance at one or more of the spherical connection points, the range of rotational motion can be increased without creating a side load on the linear actuators.

By removing the line of sight requirement necessary to utilize optical alignment tools, the alignment adjustment operation can be performed with the equipment closed, maintaining the environmental protection afforded by the covers, and permits alternative construction techniques and arrangements not presently available.

Figure 3:
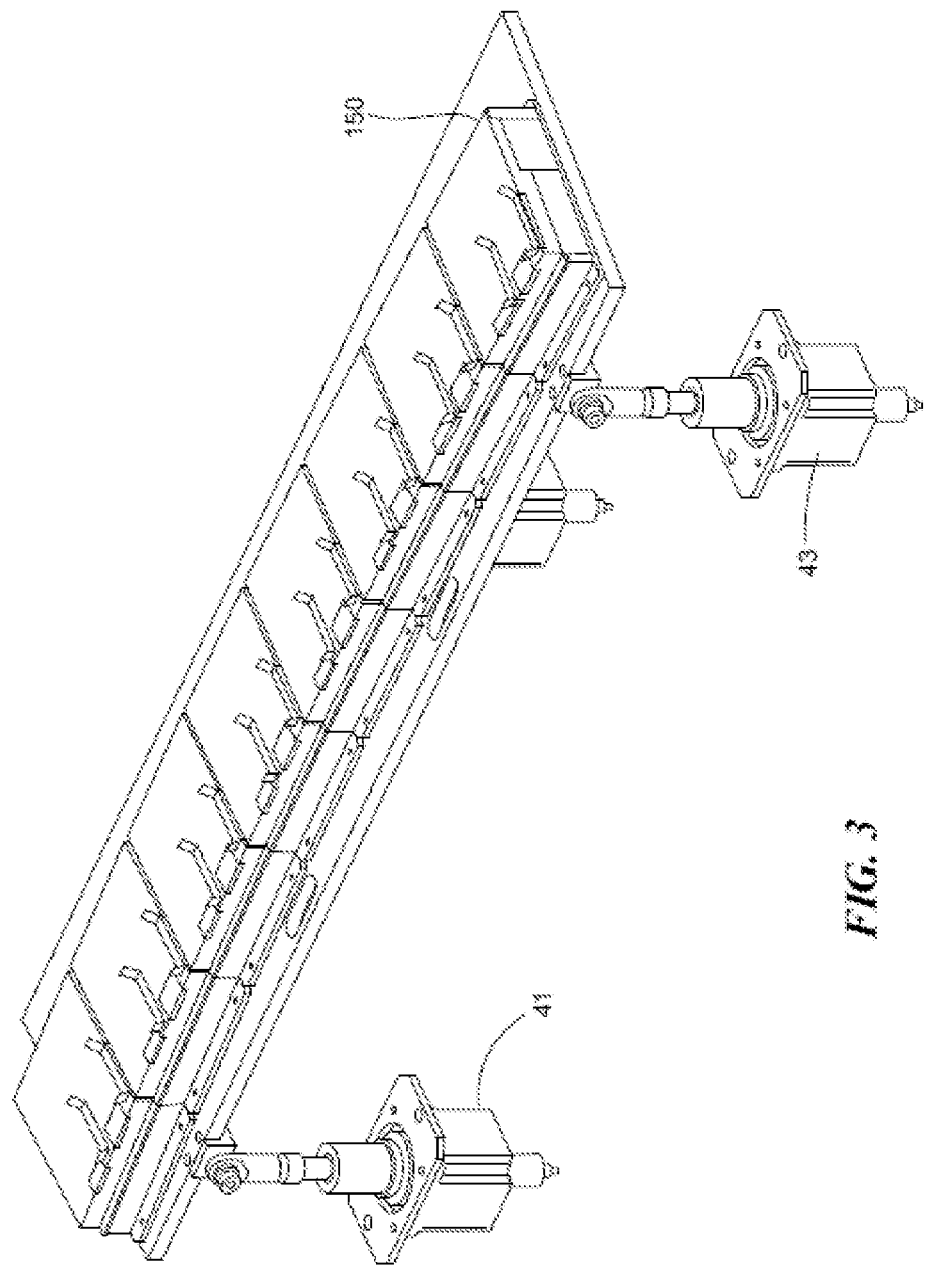
FIG. 3 depicts an arrangement of the three linear actuators with spherical rod ends used to mount the detector module support plate, in accordance with embodiments of the present invention.

The actuation mechanism is adapted to translate and/or rotate the detector modules in one or more axis of motion with respect to the x-ray beam plane. Where reference is made, for heuristic purposes, to linear actuators, it is to be understood that other forms of mechanisms capable of similar reorientations are within the scope of the present invention. A detector module or group of modules is mounted to a common detector base plate for planar support, as shown in FIG. 3. The base plate is supported by three linear actuators using spherical connection elements to provide the necessary degrees of freedom to permit the base plate to translate and rotate with respect to the line of action of the three linear actuators.

For small arrays of modules, a single base plate is preferred. For larger arrays, the base plate is preferably divided into subsections, and a mechanism is provided to support and position each sub section individually. Depending on the range of motion desired, additional compliance in one or more directions may be incorporated at the spherical connection points to prevent side load forces from developing on the linear actuators when the base plate is rotated out of plane.

The controls portion of the invention consist of three axis controllers that operate the actuators individually and also simultaneously in specific groups of two and three, to permit the detector base plate to be manipulated along particular motion paths. A controls interface, which is either under the control of the equipment technician or under automatic supervisory software control, is responsible for monitoring the signal feedback from a single detector element or a group of detector elements. The results of the changes in signal feedback can then be utilized by the technician or software monitoring system to determine either the optimum actuator positions to align the array or for the assessment of the beam forming system and its alignment.

FIG. 3 shows one basic arrangement of the three linear actuators with spherical rod ends used to mount the detector module support plate. The rear actuator employs a shoulder screw that is longer than the spherical rod end is thick to permit a larger range of rotation without inducing lateral force on the actuators.

Figure 4:
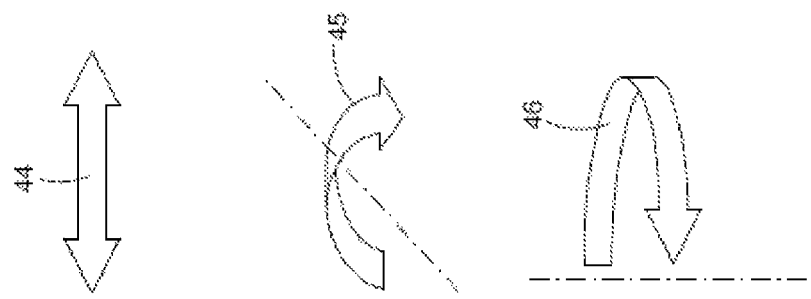
FIG. 4 shows types of motion achieved by operating different actuators in unison, and the type of resolution achievable, in accordance with embodiments of the present invention.
Figure 4:
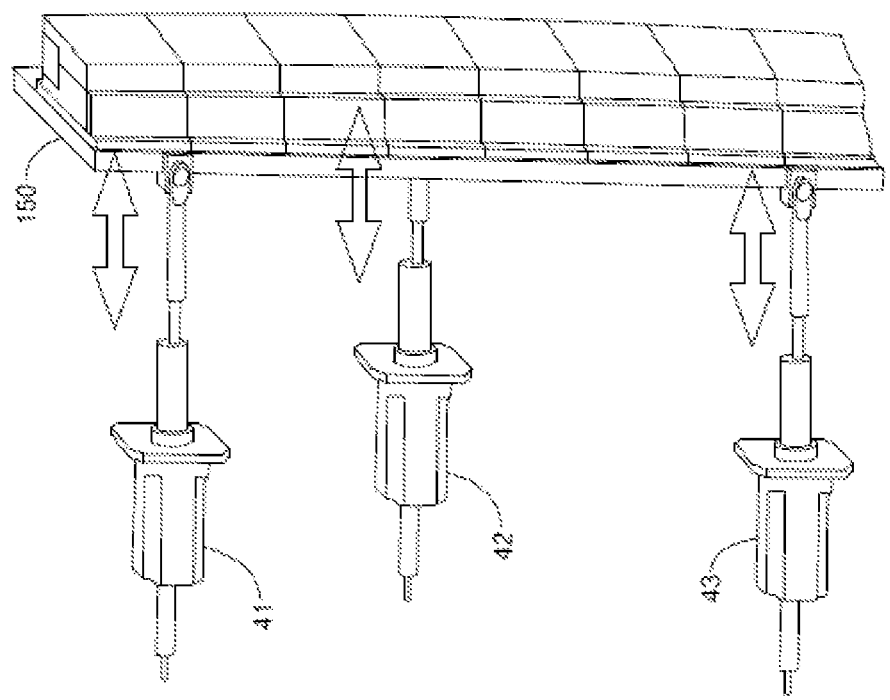

FIG. 4 shows the type of motions that can be achieved by operating one or more of linear actuators 41, 42, and 43, alone or in groupings, and the type of resolution achievable using commercially available actuators. Each of linear actuators 41, 42, and 43 operates on detector plate 150. Motion of the three actuators in unison provides a translation of detector plate 150, parallel to the direction indicated by arrow 44. In a typical embodiment of the invention, total travel is ±1.0", in increments of 0.0005". Roll of detector plate 150 in the sense indicated by arrow 45 may be achieved by fixing actuator 42, and by actuating actuators 41 and 43 in opposite directions. A range of ±3.2° may be covered in a typical embodiment of the invention, with an increment of arctan (0.0005"/18"), corresponding to 5.7 seconds of arc. Yaw of detector plate 150 in the sense indicated by arrow 46 may be achieved by fixing actuators 41 and 42 and by actuating actuator 43. A range of ±4.4° may be covered in a typical embodiment of the invention, with an increment of arctan (0.0005"/13.13"), corresponding to 7.85 seconds of arc.

The detector alignment system described herein may advantageously permit higher precision adjustments than practically achieved using manual adjustments, as well as adjustment while the source is energized using the detector module for feedback. In its simplest form, the adjustments are controlled individually by the technician based on the observed signal level or levels of the modules being adjusted at the initial startup of the machine. The control of the actuators may be remote, in certain embodiments.

The preferred method of automatic alignment is one that uses a figure-of-merit function based on the measured or simulated detector response function. A set of boundaries in the displacement/movement of the actuators are set based on the mechanical properties of the system, then a maximization algorithm (such as, for example, the method of steepest descent) is run within that parameter space to find the optimum position.

Control of the actuators may also be semi-automated via software that sweeps the actuators through a prescribed routine that determines the optimum location for that detector module or group of modules. The use of the actuator alignment system may be performed at equipment startup or after major service that may have influenced the alignment of the system Software and controls for the actuators may also be fully incorporated into the equipment and may be used in both a manual (i.e., controlled by a technician) or automatic (computer controlled) mode whenever necessary. The software and controls may be utilized during the equipment startup routine to verify and adjust the position of the actuators and assess overall equipment condition.

Dynamic Alignment Adjustments.

The software and controls may also be utilized actively during operation of the equipment to cancel out or reduce the effects of equipment drive train load, wind loads, thermal changes, grade changes, or other detectable conditions that can affect the alignment of the machine or detectors in a deterministic way.

In further embodiments of the invention, the actuator, motor, or adjustment power source and any or all portions of the control system may be removable to reduce system cost or weight once the alignment operation is performed.

Where examples presented herein involve specific combinations of method acts or system elements, it should be understood that those acts and those elements may be combined in other ways to accomplish the same objective of x-ray inspection. Additionally, single device features may fulfill the requirements of separately recited elements of a claim. The embodiments of the invention described herein are intended to be merely exemplary; variations and modifications will be apparent to those skilled in the art. All such variations and modifications are intended to be within the scope of the present invention as defined in any appended claims.

What is claimed is:

1. A method for deriving one or more specified characteristics of an inspected object, the method comprising:
   a. activating a single source of energetic particles to generate a fan beam of energetic particles;
   b. detecting the fan beam of energetic particles with a plurality of detector modules, the plurality of detector modules distributed among a plurality of detector plates arcuately disposed substantially in a single plane at a distance from the single source of energetic particles, each of the detector modules comprising a plurality of detector elements, and a subset plurality of the detector modules disposed on one remotely activated alignment plate of a plurality of remotely activated alignment plates, c. aligning the plurality of detector modules by activation of the plurality of alignment plates on the basis of a detection signal generated by each of the detector elements due to activation of the single source of energetic particles such that each of the plurality of detector elements detects a unique portion of the fan beam;

d. irradiating the inspected object with a plurality of pulses of penetrating radiation;

e. detecting the penetrating radiation after traversal of the inspected object thereby and generating an imaging signal; and f. processing the imaging signal to derive an image of the inspected object.

2. A method in accordance with claim 1, wherein each remotely activated alignment plate is identical to a distinct detector plate of the plurality of detector plates.

3. A method in accordance with claim 1, further comprising moving the source and the plurality of detector elements with respect to the container in a direction substantially transverse to the fan beam.

4. A method in accordance with claim 1, wherein activating the single source of energetic particles includes activating a linac.

* * * * *